United States Patent [19]

Turner et al.

[11] 4,304,260
[45] Dec. 8, 1981

[54] FLEXIBLE DIAPHRAGM VALVE DEVICE

[76] Inventors: Charles R. Turner, 1106 Paper Mill Rd., Philadelphia, Pa. 19118; Roger S. Turner, 620 Carpenter La., Philadelphia, Pa. 19119

[21] Appl. No.: 90,471

[22] Filed: Nov. 1, 1979

[51] Int. Cl.³ .............................................. A61M 5/14
[52] U.S. Cl. .................................. 137/613; 251/61.1; 251/331; 128/214 R; 222/450
[58] Field of Search .............................. 251/331, 61.1; 128/214 R, 214 E; 222/450, 209, 212, 448, 449, 518, 559

[56] References Cited

U.S. PATENT DOCUMENTS

| | | | |
|---|---|---|---|
| 3,286,977 | 11/1966 | Miottel | 251/331 |
| 3,685,789 | 8/1972 | Puster et al. | 251/367 |
| 3,693,611 | 9/1972 | Ploss | 251/61.1 |
| 3,718,552 | 2/1973 | Krackman | 251/61.1 |
| 3,727,623 | 4/1973 | Robbins | 251/331 |
| 3,743,245 | 7/1973 | Demier, Sr. | 251/331 |
| 4,121,584 | 10/1978 | Turner et al. | 222/450 |
| 4,142,523 | 3/1979 | Stegeman | 137/613 |
| 4,181,245 | 1/1980 | Garret et al. | 251/331 |
| 4,204,538 | 5/1980 | Cannon | 128/214 R |
| 4,223,813 | 9/1980 | Garrett et al. | 251/61.1 |

Primary Examiner—A. Michael Chambers
Attorney, Agent, or Firm—John B. Sowell

[57] ABSTRACT

A valve device for a metering unit is provided with a planar sheet flexible diaphragm adapted to be formed in the area over the valve seat by placing the valve cover on the valve body with the flexible diaphragm therebetween. Means for forming the planar sheet flexible diaphragm over the valve area into an arcuate-shaped fluid channel portion are provided on the valve case.

8 Claims, 9 Drawing Figures

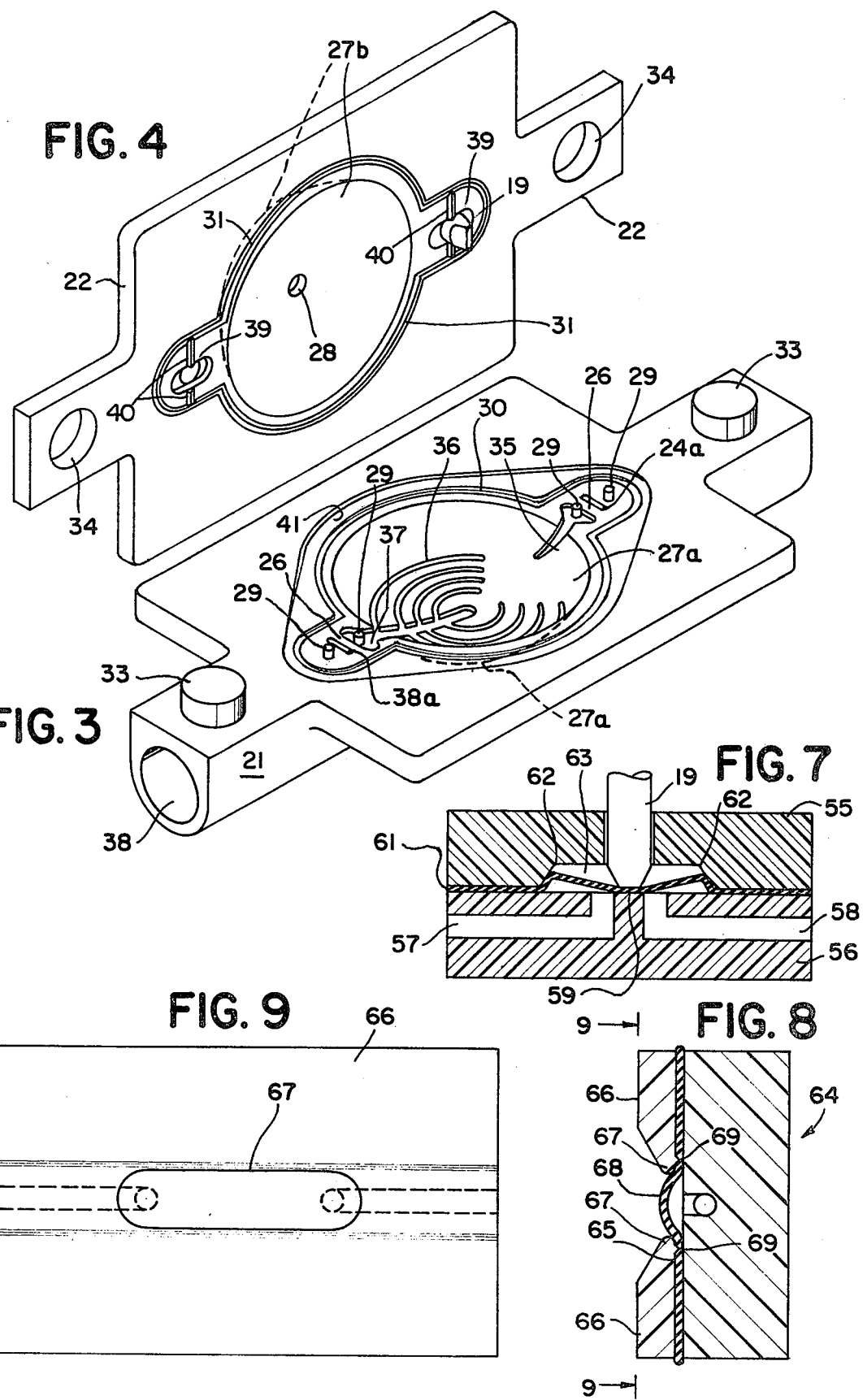

FLEXIBLE DIAPHRAGM VALVE DEVICE

BACKGROUND OF THE INVENTION

1. Field of the Invention

The present invention relates to a flexible diaphragm valve device and more particularly to valve devices of the type which are employed in metering units which are adapted to be used with intravenous (I.V.) delivery sets.

2. Description of the Prior Art

Heretofore, flexible diaphragm valve devices for metering units were known. In our U.S. Pat. No. 4,121,584 filed Oct. 15, 1976, we described an I.V. metering unit having a flexible diaphragm valve device which employed a polyurethane diaphragm. The diaphragm of this metering unit was permanently formed over the valve seat area and over the metering chamber area by heat forming. The preformed areas were difficult to align precisely with the recessed areas in the valve case. When the preformed portions of the diaphragm do not exactly align and fit the corresponding recessed areas in the valve case, the diaphragm was found to be prone to early failure.

Planar or flat sheet diaphragms have been used in valve devices in cooperation with recessed valve seats. It is known that flat diaphragms cooperating with recessed valve seats are operable. However, valves of such construction tend to be subject to early failure due to the characteristic tendency of rubber to rupture easily when it is under tension and subject to frictional scrubbing as occurs with diaphragms cooperating with recessed valve seats. Attempts to remedy this shortcoming have proven costly and have introduced new problems such as increasing the energy required for valve actuation.

It would be desirable to eliminate the problems of the prior art flexible diaphragm valve devices in a simpler and cheaper structure while retaining the ease of actuation and durability of the valve described in our U.S. Pat. No. 4,121,584.

SUMMARY OF THE INVENTION

It is an object of the present invention to provide a novel flexible diaphragm valve device which is simple and easy to manufacture.

It is another object of the present invention to provide a planar sheet flexible diaphragm valve device which embodies the desirable features of a preformed sheet flexible diaphragm valve device as described in our U.S. Pat. No. 4,121,584.

It is a specific object of the present invention to provide a novel valve case which when assembled forms a predetermined size and shape raised arcuate-shaped portion in the flat diaphragm over the valve seat area.

It is an another object of the present invention to provide a novel valve device designed for use in a highly reliable, low cost disposable I.V. metering unit.

It is a further object of the present invention to provide valves for an I.V. metering unit which are so easily actuated that they can be operated thousands of times from the energy of a small dry cell battery such as a nine volt transistor battery.

Accordingly, there is provided a flexible diaphragm valve device having a valve case comprising a valve body and a valve cover adapted to be mounted on the valve body. The valve case is provided with novel support means which forms a flexible diaphragm between the valve cover and the valve body to provide raised arcuate-shaped portions of the planar diaphragm over the valve seats. Actuation of the valve by compressively collapsing the arcuate-shaped portion of the flexible diaphragm to engage it with the valve seat causes little or no scrubbing action of the valve actuator pin upon the diaphragm and eliminates the severe tensile stresses of the diaphragm which are characteristic of prior art planar sheet diaphragm valve devices.

BRIEF DESCRIPTION OF THE DRAWINGS

FIG. 3 is a perspective view of the preferred embodiment metering unit valve body showing the valve seats, the diaphragm support means and the connecting fluid passageways;

FIG. 4 is a perspective view of the preferred embodiment metering unit valve cover adapted to be mounted on the valve body of FIG. 3;

FIG. 7 is an enlarged section in elevation of another modified embodiment planar sheet flexible diaphragm valve device;

FIG. 8 is an enlarged section in elevation of yet another modified embodiment planar sheet flexible diaphragm device; and FIG. 9 is an enlarged side or top view of the embodiment of FIG. 8.

DESCRIPTION OF THE PREFERRED EMBODIMENT

Figure 1:
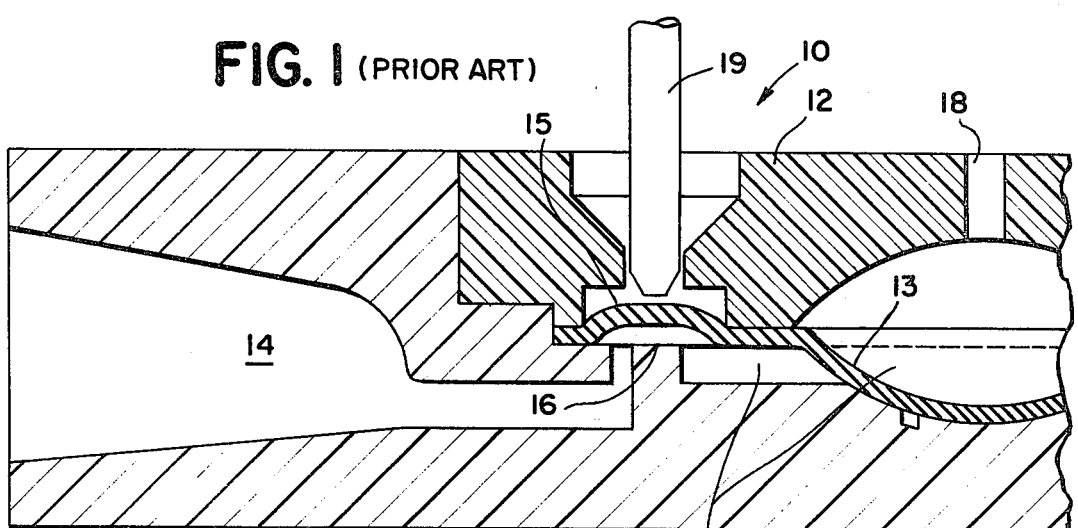
FIG. 1 is an enlarged section in elevation of a prior art preformed flexible diaphragm valve device.

Refer now to FIG. 1 showing a flexible diaphragm valve device having a preformed flexible diaphragm. Valve case 10 comprises a lower valve body 11 and an upper valve cover 12. Sandwiched and trapped between the valve cover 12 and the valve body 11 is a flexible diaphragm 13 which is made of polyurethane preformed by heat forming. Fluid entering the inlet passageway 14 rises under the preformed raised valve portion 15 of preformed flexible diaphragm 13 and passes over the valve seat 16 where it passes into the recessed metering chamber portion 17 of the lower valve body 11. The normally opened valve causes little or no pressure loss and the fluid pressure is sufficient to move the preformed portion of the flexible diaphragm 13 in the metering chamber upward. Air vent 18 is provided to permit the flexible diaphragm 13 to move upward in FIG. 1 until restricted by the recess in the valve cover. After the metering chamber is full, a valve actuator pin 19 is moved downward to engage the preformed raised valve portion 15 of diaphragm 13 against valve seat 16 and close off the flow of fluid into the metering chamber. It will be understood that a similar outlet valve (not shown) is connected to the metering chamber. The outlet valve is opened when the inlet valve shown is closed and the gravitational pressure of the fluid in the metering chamber causes the fluid to flow out of the metering chamber into the outlet fluid passageway (not shown). This prior art flexible diaphragm valve device employed a thin and flexible polyurethane diaphragm which was heat formed over the valve seat and metering chamber areas. It was found that it was difficult and costly to align the thin and flexible diaphragm precisely in the recessed areas of the valve body. When mismatches of the recessed areas and the preformed areas occurred in assembly, the diaphragm was found to be prone to early failure.

Figure 2:
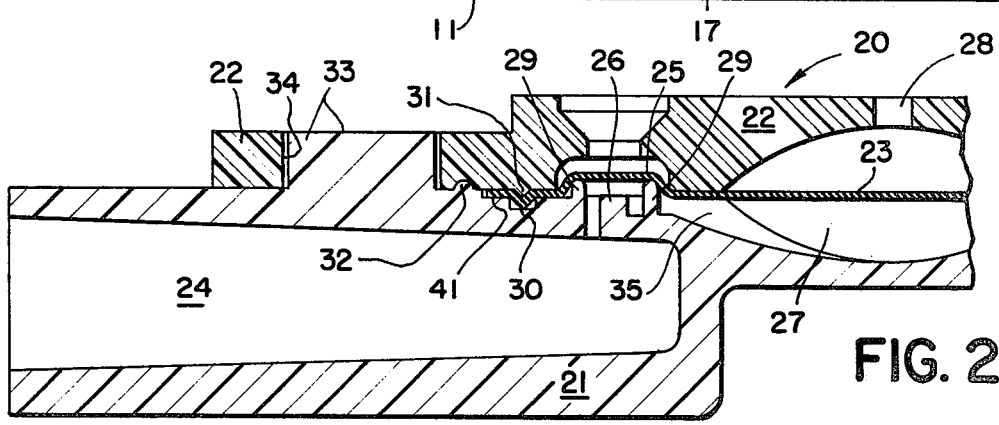
FIG. 2 is an enlarged section in elevation of the preferred embodiment planar sheet flexible diaphragm valve device.

Refer now to FIG. 2 showing a preferred embodiment of the present invention. Valve case 20 comprises a lower valve body 21 and an upper valve cover 22 which is adapted to be mounted thereon and to entrap a planar sheet flexible diaphragm 23 therebetween. Fluid entering passageway 24 is permitted to enter the arcuate-shaped raised portion 25 of the flexible diaphragm and to pass over the valve seat 26 where it enters the metering chamber 27. The pressure of the fluid entering the metering chamber is sufficient to deform the flexible diaphragm 23 so that it engages the upper recess portion of the metering chamber in the valve cover 22. Air vent 28 is provided to permit the metering chamber 27 to be filled with fluid. It will be understood that the arcuate raised portion 25 of the planar flexible diaphragm was normally and originally flat before the valve cover 22 was mounted on the valve body 21 which caused the portion 25 to become arcuate and raised over the valve seat 26 by projections 29 which form support means for forming the planar sheet flexible diaphragm 23 over the valve seat area 26. It will be understood that fluid flowing over the valve seat 26 may flow around projections 29. A recess channel 30 in valve body 21 cooperates with a protrusion 31 on valve cover 22 to entrap and hold the edges of the flexible diaphragm 23 around the valve seat area 26. Valve cover 22 may be attached to valve body 21 by ultrasonic bonding employing a raised bonding ring 32 or by known adhesive bonding techniques or mechanical means.

Refer now to FIGS. 3 and 4 showing the valve body 21 and valve case 20 in a perspective view with the planar flexible diaphragm 23 removed. The valve cover 22 may be precision aligned with the valve body 21 by locating pins 33 which cooperate with locating recesses 34. Fluid entering the inlet passageway 24 of valve body 21 enters the valve chamber area at termination point or port 24a where it flows across the flat valve seat 26 and flows around protrusion support means 29 and enters the shaped recess 35 of the metering chamber 27a. The metering chamber 27a in valve body 21 is provided with tree-shaped recessed scavaging rings 36 which prevent the flexible diaphragm 23 from trapping fluid in the chamber 27a. Fluid in the metering chamber 27 flows to the shaped recess 37 surrounding the protrusion 29. The fluid flows over the outlet valve seat 26 and enters the outlet port 38a which is connected to the outlet passageway 38.

It will be understood that in the preferred mode of operation fluid is permitted to enter inlet passageway 24 and to fill the metering chamber 27 while the upper valve is opened and the lower valve is closed. The metering chamber is emptied by reversing the sequence of valve operations wherein the upper valve is closed and the lower valve is opened. A valve actuator pin 19 is shown in FIG. 4 extending through its guide in the valve cover 22. An oval shaped recess 39 surrounds the valve actuator pin 19 and is made large enough to receive the arcuate-shaped raised portion 25 of the flexible diaphragm 23 without engaging same. Preferably, the recess 30 shown on the valve body 21 extends completely around both valve seat areas 26 and the metering chamber 27. The raised mating protrusion 31 on the valve cover 22 likewise extends completely around the metering chamber 27 in the upper valve cover and is adapted to entrap the edge portions of the flexible diaphragm 23 in recess 30. Preferably, short spurs 40 extend from protrusions 31 to the edges of recesses 39. The inwardly extending spurs 40 prevent leakage around the sides of the valve seats 26. The planar sheet flexible diaphragm 23 preferably is the same shape as and slightly smaller than the film positioning recess 41 shown in lower valve body 21. Accordingly, the flat planar sheet may be easily placed within the recess 41 and the operation of mounting the valve cover 22 onto the lower valve body 21 will stretch, clamp and seal the edges of the flexible diaphragm 23 between the recess 30 and protrusion 31 as explained hereinbefore. The excess material of the flexible diaphragm 23 which occurs outside of the recess 30 serves no function other than to provide sufficient material to avoid any necessity for critical alignment of the flexible diaphragm 23 onto the lower valve body 21.

Figure 6:
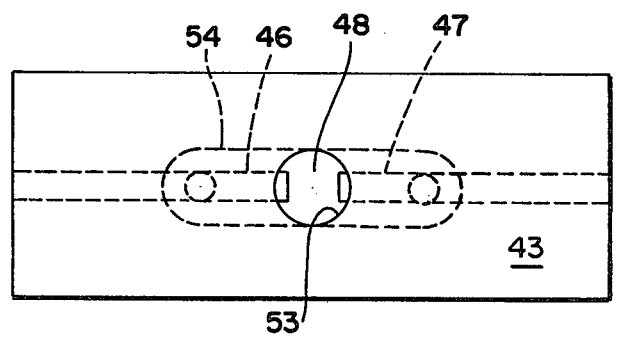
FIG. 6 is an enlarged top view of the embodiment of FIG. 5.
Figure 5:
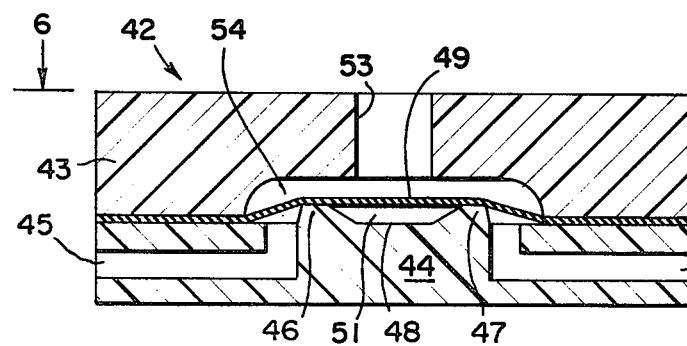
FIG. 5 is an enlarged section in elevation of a modified embodiment planar sheet flexible diaphragm valve device.

Refer now to FIGS. 5 and 6 showing a modified embodiment planar sheet flexible diaphragm valve device 42. Upper valve cover 43 is shown mounted on lower valve body 44. Inlet passageway 45 terminates opposite a protrusion or diaphragm support means 46. Support means 46 and 47 have a valve seat 48 therebetween. When the raised arcuate portion 49 of the flexible diaphragm 50 is normally out of engagement with the valve seat 48, fluid is permitted to pass through the open fluid channel 51 formed by the arcuate portion 49 and the valve seat 48 and to enter into the outlet passageway 52. It will be understood that the valve actuator pin which operates in guide 53 is not shown. While the recesses and protrusions for entrapping the flexible diaphragm are not shown in FIG. 5 it will be understood that such structure as shown and explained with regards to FIGS. 1 to 4 may be employed with the valve device shown in FIG. 5.

FIG. 6 is a top view of the valve device of FIG. 5 and is shown with the flexible diaphragm removed so that the support means 46, 47 and valve seat 48 may be more clearly illustrated.

The edges of the recess 54, shown in dotted lines, clamp the flexible diaphragm 49 and cooperate to form an arcuate-shaped portion with support means 46, 47. Further, it will be understood that the arcuate raised portion 49 of the flexible diaphragm 50 is raised only slightly above the valve seat 48 and the clearances and dimensions shown are for purposes of illustration and not intended to be actual dimensions.

Refer now to FIG. 7 showing another embodiment of the flexible diaphragm valve device. Upper valve cover 55 is mounted on lower valve body 56. Inlet passageway 57 and outlet passageway 58 terminate closely adjacent the flat valve seat 59 in lower valve body 56. The planar sheet flexible diaphragm 61 is tension or compression formed in the recess 63 of the upper valve cover 55. Preferably the recess 63 is arcuate shaped and the flexible diaphragm 61 is adhesively bonded at the location portions 62. When valve actuator pin 19 is moved downward to close the valve, the center of the arcuate-shaped portion collapses and engages the valve seat in a manner which causes no significant friction or harmful stress of the flexible diaphragm 61.

Refer now to FIGS. 8 and 9 showing yet another modified embodiment of the flexible diaphragm valve device. Valve body 64 supports a flexible diaphragm 65 which is compressed by valve cover 66 so as to cause the material of flexible diaphragm 65 to flow into the aperture or opening 67 in valve cover 66 so as to form the arcuate raised portion 68 of the flexible diaphragm 65. A flexible diaphragm 65, even though made from a highly resilient material such as latex rubber and/or synthetic rubbers, is substantially incompressible. When the valve cover 66 is applied with sufficient force to the valve body 64 by means not shown the substantially incompressible flexible diaphragm material flows out from under the valve cover and into the aperture or opening area 67 so as to form the desired arcuate raised portion 68. Protrusions 69 control the amount of compressive force applied to diaphragm 65, thus, aid in controlling the flow into area 67.

Having explained a preferred embodiment and modifications thereof of the diaphragm valve device it will be understood that the tip of the valve actuator pin 19 is shaped to avoid scrubbing and puncturing the flexible diaphragm. By providing the arcuate raised shape in the portion of the flexible diaphragm directly over the valve seat the raised portion of the flexible diaphragm displaced by the valve actuator pin 19 is restored to its original planar flat shape when the valve is closed.

Having explained that the flexible diaphragm may be laid within the film positioning recess 41 provided in the valve body 21 shown in FIG. 3, it will be understood that the flexible diaphragm extends over the metering chamber recess 27a. In FIGS. 5 and 6, a vacuum may be applied to guide holes 53 to hold the flexible diaphragm 50 in the valve cover 43 during assembly. This latter method is also capable of drawing the flexible diaphragm into recesses like recess 54 of FIG. 5 and recess 63 of FIG. 7. It will be understood that the arcuate raised portion of the flexible diaphragm has been shown in exaggerated form to better illustrate the invention.

It has been found that in adapting the valve of the present invention to an I.V. metering unit of the type described in application Ser. No. 732,946, now U.S. Pat. No. 4,121,584, that a latex flexible diaphragm having a thickness of 0.006 inches functions well in conjunction with a valve seat width of 0.093 inches and a film arch height of 0.030 inches. It will be understood that for any given diaphragm thickness, there will be a corresponding limit to the height-to-width ratio of the arch of the flexible diaphragm which can be used without folding of the diaphragm during valve closure. Folding or fold over of the flexible diaphragm causes premature failure or valve leakage.

In the preferred mode of operation, the valve actuator pin 19 collapses the arcuate raised portion of the flexible diaphragm in a manner which restores the formed arcuate raised shaped portion of the flexible diaphragm to its original flat planar shape with substantially no stretch under the valve actuator pin. The actuator pin merely compresses the flexible diaphragm against the flat valve seat thus eliminating scrubbing and tension stresses in the flexible diaphragm.

The force required to effect closure of the valve of the present invention is under five grams whereas a force of from twenty-five to forty grams is typically required to fully close prior art planar sheet valves of the type having recessed valve seats and which are designed to permit flow equal to the present invention.

Tests of valves made in accordance with the teachings of the present invention have proven them to be capable of reliable operation over many hundreds of thousands of operating cycles. Further, the very small forces required for valve actuation of the present invention permits several months of continuous operation without the requirement for a battery change.

We claim:

1. A valve device for controlling the flow of fluid comprising:
   a valve case,
   a pair of fluid passageways in said valve case terminating adjacent to a surface on said valve case,
   a valve seat on said surface of said valve case interposed between said fluid passageways,
   support means protruding from said valve case comprising a discrete isolated raised element closely adjacent to said valve seat,
   a planar sheet flexible diaphragm mounted on said valve case and being formed by said support means including said discrete isolated raised element to provide a small elongated raised arcuate shaped open fluid conducting channel portion juxtaposed over said valve seat, said support means and said fluid passageways,
   said raised arcuate-shaped portion of said flexible diaphragm which is over said valve seat being collapsible and engagable with said valve seat to close said open fluid conducting channel portion between said fluid passageways, said discrete isolated raised element disposed between said valve seat and one of said passageways such that fluid flows around said element in the open position.

2. A valve device as set forth in claim 1 wherein said support means comprises a plurality of discrete isolated raised elements, at least one on each side of said valve seat for forming said arcuate-shaped fluid channel in said diaphragm between said fluid passageways.

3. A valve device as set forth in claim 2 wherein said elements and said valve seat form parts of the same member of the valve case.

4. A valve device as set forth in claim 1 wherein said valve case comprises a valve cover adapted to be mounted on a valve body,
   said valve cover being adapted to squeeze portions of said planar sheet flexible diaphragm around said valve seat to form said arcuate-shaped open fluid channel portion.

5. A valve device as set forth in claim 4 wherein said valve cover is provided with form controlling protrusions and said valve cover is provided with a recessed cavity into which said arcuate-shaped portion of said flexible diaphragm is raised.

6. A valve device as set forth in claim 4 wherein said valve cover comprises an elongated opening adapted to fit over said arcuate-shaped portion and to clamp said planar sheet flexible diaphragm around said arcuate shaped portion.

7. A fluid metering unit for controlling the flow of fluid comprising:
   a valve case,
   valve means comprising an inlet valve and an outlet valve in said valve case, each said valve comprising,
   a pair of fluid passageways in said valve case terminating at a valve seat in said valve case,
   a planar sheet flexible diaphragm,
   support means cooperating with said planar sheet flexible diaphragm for forming and supporting a small elongated portion of said flexible diaphragm to provide an arcuate channel shaped portion in said planar sheet and a fluid conducting channel juxtaposed said valve seat and said pair of fluid passageways, said support means protruding from said valve case as discrete isolated raised elements located closely adjacent to said valve seat in said fluid conducting channel, said arcuate channel shaped portion of said flexible diaphragm juxtaposed said valve seat being adapted to be engaged into contact with said valve seat to prevent flow of fluid through said fluid conducting channel at least one of said discrete isolated raised elements being disposed between said valve seat and one of said passageways such that fluid flows around said one element in the open position, and a metering chamber intermediate said inlet valve and said outlet valve which cooperates with said valves to form a fluid metering unit.

8. A fluid metering unit as set forth in claim 7 wherein said arcuate channel shaped portion of said flexible diaphragm juxtaposed said valve seats is adapted to be deformed and returned to its original planar shape along a line extending across said valve seat upon actuation by an actuation pin.

* * * * *